US009622893B2

(12) United States Patent
Huser

(10) Patent No.: US 9,622,893 B2
(45) Date of Patent: Apr. 18, 2017

(54) APPARATUS AND METHOD FOR IMPROVED DEPLOYMENT OF ENDOVASCULAR GRAFTS

(71) Applicant: Cook Medical Technologies LLC, Bloomington, IN (US)

(72) Inventor: Matthew S. Huser, West Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 412 days.

(21) Appl. No.: 13/970,861

(22) Filed: Aug. 20, 2013

(65) Prior Publication Data
US 2014/0180386 A1   Jun. 26, 2014

Related U.S. Application Data

(60) Provisional application No. 61/739,888, filed on Dec. 20, 2012.

(51) Int. Cl.
A61F 2/06     (2013.01)
A61F 2/966    (2013.01)
A61F 2/95     (2013.01)

(52) U.S. Cl.
CPC ....... A61F 2/966 (2013.01); A61F 2002/9511 (2013.01); A61F 2002/9665 (2013.01)

(58) Field of Classification Search
CPC .. A61F 2/95; A61F 2/962; A61F 2/966; A61F 2002/9511; A61F 2002/9665; A61F 2/013; A61F 2/01; A61F 2/2427; A61F 2/2418; A61M 25/0147
USPC ........... 623/1.1, 1.11–1.15, 1, 23, 235, 2.11, 623/1.23; 606/108, 200
See application file for complete search history.

(56) References Cited

U.S. PATENT DOCUMENTS

| 4,878,906 A | 11/1989 | Lindemann et al. |
| 4,913,141 A | 4/1990 | Hillstead |
| 5,019,085 A | 5/1991 | Hillstead |
| 5,405,378 A | 4/1995 | Strecker |
| 5,693,083 A | 12/1997 | Baker et al. |

(Continued)

FOREIGN PATENT DOCUMENTS

| EP | 2517672 A1 | 10/2012 |
| JP | 2006-346350 | 12/2006 |

(Continued)

OTHER PUBLICATIONS

Extended European Search Report for EP 13275314 dated Apr. 15, 2014 (5 pages).

(Continued)

Primary Examiner — Darwin Erezo
Assistant Examiner — Erich Herbermann
(74) Attorney, Agent, or Firm — Brinks Gilson & Lione

(57) ABSTRACT

Apparatus and methods for facilitating deployment of an implantable medical device including a stent graft. A restraining device, such as cord or suture, holds at least the proximal end of the stent in a radially inwardly compressed configuration during delivery to a desired location within the lumen of a patient's vessel. Withdrawal of one or more trigger wires facilitates the release and removal of the restraining cord from the proximal end of the stent so as to allow the stent to become fully deployed within vessel.

20 Claims, 12 Drawing Sheets

(56) References Cited

U.S. PATENT DOCUMENTS

| | | | |
|---|---|---|---|
| 5,843,158 A | 12/1998 | Lenker et al. | |
| 5,919,225 A | 7/1999 | Lau et al. | |
| 6,224,627 B1 | 5/2001 | Armstrong et al. | |
| 6,398,758 B1 | 6/2002 | Jacobsen et al. | |
| 6,524,335 B1* | 2/2003 | Hartley | A61F 2/07 623/1.12 |
| 6,551,356 B2 | 4/2003 | Rousseau | |
| 6,562,064 B1 | 5/2003 | deBeer | |
| 6,565,597 B1 | 5/2003 | Fearnot et al. | |
| 6,692,521 B2 | 2/2004 | Pinchasik | |
| 6,716,238 B2 | 4/2004 | Elliott | |
| 6,964,677 B2 | 11/2005 | Osypka | |
| 6,997,939 B2 | 2/2006 | Linder et al. | |
| 7,160,318 B2 | 1/2007 | Greenberg et al. | |
| 7,393,357 B2 | 7/2008 | Stelter et al. | |
| 7,611,528 B2 | 11/2009 | Goodson, IV et al. | |
| 7,803,177 B2 | 9/2010 | Hartley et al. | |
| 7,909,863 B2 | 3/2011 | Hartley et al. | |
| 8,043,356 B2 | 10/2011 | Kölbel et al. | |
| 8,192,351 B2 | 6/2012 | Fishler et al. | |
| 8,323,328 B2 | 12/2012 | Martin et al. | |
| 8,328,861 B2* | 12/2012 | Martin et al. | 623/1.12 |
| 8,535,344 B2 | 9/2013 | Linder et al. | |
| 2001/0041925 A1 | 11/2001 | Konya et al. | |
| 2002/0007208 A1 | 1/2002 | Strecker | |
| 2002/0029077 A1 | 3/2002 | Leopold et al. | |
| 2003/0050684 A1 | 3/2003 | Abrams et al. | |
| 2003/0233140 A1 | 12/2003 | Hartley et al. | |
| 2004/0073289 A1 | 4/2004 | Hartley | |
| 2004/0106978 A1 | 6/2004 | Greenberg et al. | |
| 2004/0138734 A1 | 7/2004 | Chobotov et al. | |
| 2004/0193178 A1 | 9/2004 | Nikolchev | |
| 2004/0193244 A1 | 9/2004 | Hartley et al. | |
| 2004/0220655 A1 | 11/2004 | Swanson et al. | |
| 2005/0085890 A1 | 4/2005 | Rasmussen et al. | |
| 2005/0090887 A1 | 4/2005 | Pryor | |
| 2005/0107862 A1 | 5/2005 | Ohlenschlaeger | |
| 2005/0137701 A1 | 6/2005 | Salahieh et al. | |
| 2005/0288768 A1 | 12/2005 | Sowinski et al. | |
| 2006/0142836 A1 | 6/2006 | Hartley et al. | |
| 2006/0190070 A1 | 8/2006 | Dieck et al. | |
| 2007/0100427 A1 | 5/2007 | Perouse | |
| 2007/0198077 A1 | 8/2007 | Cully et al. | |
| 2007/0208409 A1 | 9/2007 | Quigley | |
| 2007/0233223 A1* | 10/2007 | Styrc | A61F 2/2439 623/1.11 |
| 2008/0027529 A1 | 1/2008 | Hartley et al. | |
| 2008/0140178 A1 | 6/2008 | Rasmussen et al. | |
| 2008/0294231 A1* | 11/2008 | Aguilar et al. | 623/1.11 |
| 2009/0030497 A1 | 1/2009 | Metcalf et al. | |
| 2009/0048656 A1* | 2/2009 | Wen | A61F 2/2418 623/1.12 |
| 2009/0082842 A1 | 3/2009 | Glynn | |
| 2009/0082847 A1 | 3/2009 | Zacharias et al. | |
| 2009/0099640 A1 | 4/2009 | Weng | |
| 2009/0112302 A1 | 4/2009 | Stafford | |
| 2009/0171431 A1 | 7/2009 | Swanson et al. | |
| 2009/0204202 A1 | 8/2009 | Dierking et al. | |
| 2009/0259291 A1 | 10/2009 | Kolbel et al. | |
| 2010/0010617 A1 | 1/2010 | Goodson, IV et al. | |
| 2010/0049293 A1* | 2/2010 | Zukowski | A61F 2/07 623/1.11 |
| 2010/0049294 A1* | 2/2010 | Zukowski et al. | 623/1.11 |
| 2010/0168838 A1 | 7/2010 | Hartley et al. | |
| 2010/0249896 A1 | 9/2010 | Sugimoto et al. | |
| 2010/0286768 A1 | 11/2010 | Alkhatib | |
| 2011/0178588 A1 | 7/2011 | Haselby | |
| 2011/0190865 A1 | 8/2011 | McHugo et al. | |
| 2011/0288624 A1 | 11/2011 | Roeder et al. | |
| 2012/0010696 A1 | 1/2012 | Greenberg et al. | |
| 2012/0095567 A1 | 4/2012 | Weisman et al. | |
| 2012/0277848 A1 | 11/2012 | Roeder et al. | |
| 2013/0116773 A1* | 5/2013 | Roeder et al. | 623/1.15 |
| 2013/0245743 A1 | 9/2013 | Norris | |

FOREIGN PATENT DOCUMENTS

| | | |
|---|---|---|
| WO | WO 01/74270 A2 | 10/2001 |
| WO | WO 2004/017868 A1 | 3/2004 |
| WO | WO 2004/019823 A1 | 3/2004 |
| WO | WO 2006/037086 A1 | 4/2006 |
| WO | WO 2008/066923 A1 | 6/2008 |
| WO | WO 2009/126227 A2 | 10/2009 |
| WO | WO 2010/042210 A1 | 4/2010 |
| WO | WO 2011/059707 A1 | 5/2011 |
| WO | WO 2012/058104 A1 | 5/2012 |

OTHER PUBLICATIONS

International Preliminary Report on Patentability for PCT/US2009/005890, dated Dec. 28, 2010, 6 pages.
International Search Report and Written Opinion for PCT/US2009/005890, mailed Feb. 4, 2010, 8 pages.
Canadian Office Action and Search Report for CA Application No. 2,737,438 dated Aug. 25, 2015, 3 pages.
Extended European Search Report dated Apr. 4, 2013, European Patent Application 12197088.3, European Patent Office, The Netherlands, 7 pages.
English translation of Japanese Office Action/Reason for Rejection for JP 2011-534517, dated Aug. 27, 2013, 2 pages.
Office Action for U.S. Appl. No. 12/609,066, dated Dec. 21, 2011, 8 pages.
Response to Office Action for U.S. Appl. No. 12/609,066, dated Mar. 21, 2012, 12 pages.
Office Action for U.S. Appl. No. 12/609,066, dated Apr. 10, 2012, 12 pages.
Response to Office Action for U.S. Appl. No. 12/609,066, dated Jul. 10, 2012.
Advisory Action for U.S. Appl. No. 12/609,066, dated Aug. 15, 2012, 3 pages.
Pre-Appeal Brief for U.S. Appl. No. 12/609,066, dated Sep. 7, 2012, 6 pages.
Pre-Appeal Brief Decision for U.S. Appl. No. 12/609,066, dated Apr. 30, 2013, 2 pages.
Office Action for U.S. Appl. No. 12/609,066, dated Jan. 16, 2014, 15 pages.
Response to Office Action for U.S. Appl. No. 12/609,066, dated Apr. 16, 2014, 9 pages.
Office Action for U.S. Appl. No. 12/609,066, dated May 14, 2014, 18 pages.
After Final Pilot Response for U.S. Appl. No. 12/609,066, dated Jul. 11, 2014, 11 pages.
Advisory Action and Interview Summary for U.S. Appl. No. 12/609,066, dated Aug. 12, 2014, 6 pages.
Response for U.S. Appl. No. 12/609,066, dated Sep. 15, 2014, 10 pages.
Office Action for U.S. Appl. No. 12/609,066, dated Jan. 27, 2015, 26 pages.
Response to Office Action for U.S. Appl. No. 12/609,066, dated Apr. 27, 2015, 11 pages.
Office Action for U.S. Appl. No. 12/609,066, dated May 29, 2015, 28 pages.
Response to Office Action for U.S. Appl. No. 12/609,066, dated Sep. 29, 2015, 12 pages.
Office Action for U.S. Appl. No. 13/713,517, dated Mar. 16, 2015, 20 pages.
Response to Office Action for U.S. Appl. No. 13/713,517, dated Sep. 16, 2015, 9 pages.

* cited by examiner

APPARATUS AND METHOD FOR IMPROVED DEPLOYMENT OF ENDOVASCULAR GRAFTS

RELATED APPLICATIONS

This application claims the benefit of priority of U.S. provisional application Ser. No. 61/739,888 filed on Dec. 20, 2012, which application is incorporated by reference herein in its entirety.

BACKGROUND

This invention relates generally to medical devices, and more particularly, to apparatus and methods for improved deployment of stents or other implantable medical devices.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they may have characteristics of both, depending on particular needs that are more suited to one stent type or the other. Self-expanding stents may be delivered to a target site in a patient's vascular system in a compressed configuration and subsequently expanded by removing a delivery sheath, removing trigger wires and/or releasing diameter reducing ties. Self-expanding stents expand primarily based on their own expansive force without the need for further mechanical expansion. In one example, a stent made of a shape-memory alloy such as Nitinol may allow the stent to return to a predetermined expanded configuration upon removal of a sheath or other device that maintains the stent in its compressed, pre-deployment configuration. In another example, stents made of materials such as stainless steel expand on their own accord once released from constraints holding them in their compressed state.

When an expandable stent is deployed, it is important to position it at the precise desired location within the lumen of a patient's vascular system. In some cases, as soon as sheath is withdrawn from the proximal end of the stent, the proximal end may expand in a rapid and irregular way, with the risk that one or more of the stent struts may be deformed, bent or damaged. Moreover, as the sheath slides over and beyond the distal end of the stent, the stent may move longitudinally out of position within the vessel as a result of the force of the sheath being pulled back as well as expand radially in a manner that may be difficult to control. As such, placement of the stent may be less accurate and may lead to damage of the vessel. Commonly, release devices such as trigger wires may be provided as a deployment control mechanism, which releasably couple the proximal and/or distal ends of a stent or stent-graft to a delivery catheter until the trigger wires are selectively released by the physician. Typically, one or more trigger wires are looped through a portion of the stent, such as the proximal stent apices, for example, to pull the stent closely (radially inward) against the delivery catheter. Trigger wires may also help prevent unwanted longitudinal movement of the stent during placement within a vessel and withdrawal of the sheath. Release of a trigger wire causes full radial expansion of the stent, such that the stent engages an inner wall of a duct or vessel. However, trigger wire systems can be complicated systems. The present invention presents a method and apparatus for the reduced diameter delivery of stent-grafts with controlled release and reduced deployment forces.

SUMMARY

The present disclosure provides a method and apparatus to accurately deploy a stent, stent graft and/or other implantable medical device that allows the graft to remain in a compressed configuration within a delivery system, reduces deployment force and provides a controlled release during deployment.

An apparatus for deploying a stent is disclosed. The apparatus comprises a stent delivery device having a proximal end portion and a distal end portion and at least one stent having a proximal and distal end and carried by the proximal end portion of the delivery device.

In one example, the stent is capable of assuming both an expanded configuration and a compressed configuration. A restraining device exerts a force on the stent in a radially inward direction for releasably restraining the proximal stent end in a radially inward compressed condition. The apparatus also comprises at least one release mechanism comprising a proximal end portion and a distal end portion, wherein the proximal end portion of the release mechanism is releasably coupled to the restraining device for selectively releasing the restraining device from the proximal stent end such that upon release of the restraining device, the stent proximal end can assume the radially outward expanded position.

In one example, the restraining device comprises an elongated material including, for example, a cord, string, suture, tie, wire, line or thread, which circumferentially encircles at least a portion of the stent proximal end. The plurality of proximal stent apices may comprise an aperture formed therein and the restraining device is woven or stitched through the at least one aperture. For example, the plurality of apices may each have an aperture for receiving the restraining device. In another example, selected apices have such an aperture, for instance, every other apex may have an aperture.

The apparatus may further include release mechanisms such as trigger wires. For example, the release mechanisms may include first and second trigger wires which releasably secure a portion of the restraining device to the stent delivery device. At least one of the first and second trigger wires may exert a radially inward force on at least a portion of the restraining device to resist longitudinal movement of the stent relative to the delivery device.

The apparatus further may include a guide catheter that extends at least partially between the proximal and distal end portions of the delivery device. Where the stent is mounted coaxially over and radially outside a portion of the guide catheter. The guide catheter may include at least one radially outwardly extending protrusion, such as a peg, post, hook, support or extension, for engaging the proximal end portion of the stent when the proximal stent end is in the radially inwardly compressed configuration to restrain longitudinal movement of the stent relative to the delivery device.

A method for deploying an endovascular prosthesis also is described. The method comprises the steps of inserting a delivery device carrying the prosthesis into the lumen of a body passage, the prosthesis having at least a proximal end retained in a radially inwardly compressed delivery condition by a restraining device and withdrawing a sheath from the delivery device to expose at least a portion of the prosthesis. The method further comprises withdrawing a first release mechanism from the delivery device to release the restraining device from the proximal end of the prosthesis to deploy the prosthesis in a radially outwardly expanded position and retracting the delivery device from the body passage.

DETAILED DESCRIPTION

Throughout this specification the terms proximal and proximally are used for a position or direction towards the patient's heart and the terms distal and distally are used for a position or direction away the patient's heart. The embodiments described below are in connection with the deployment of an implantable medical device, such as an endovascular prosthesis. It will be understood that the apparatus and methods can be used for deploying a range of implantable medical devices including stents, stent grafts, occlusion devices and the like.

Figure 1:
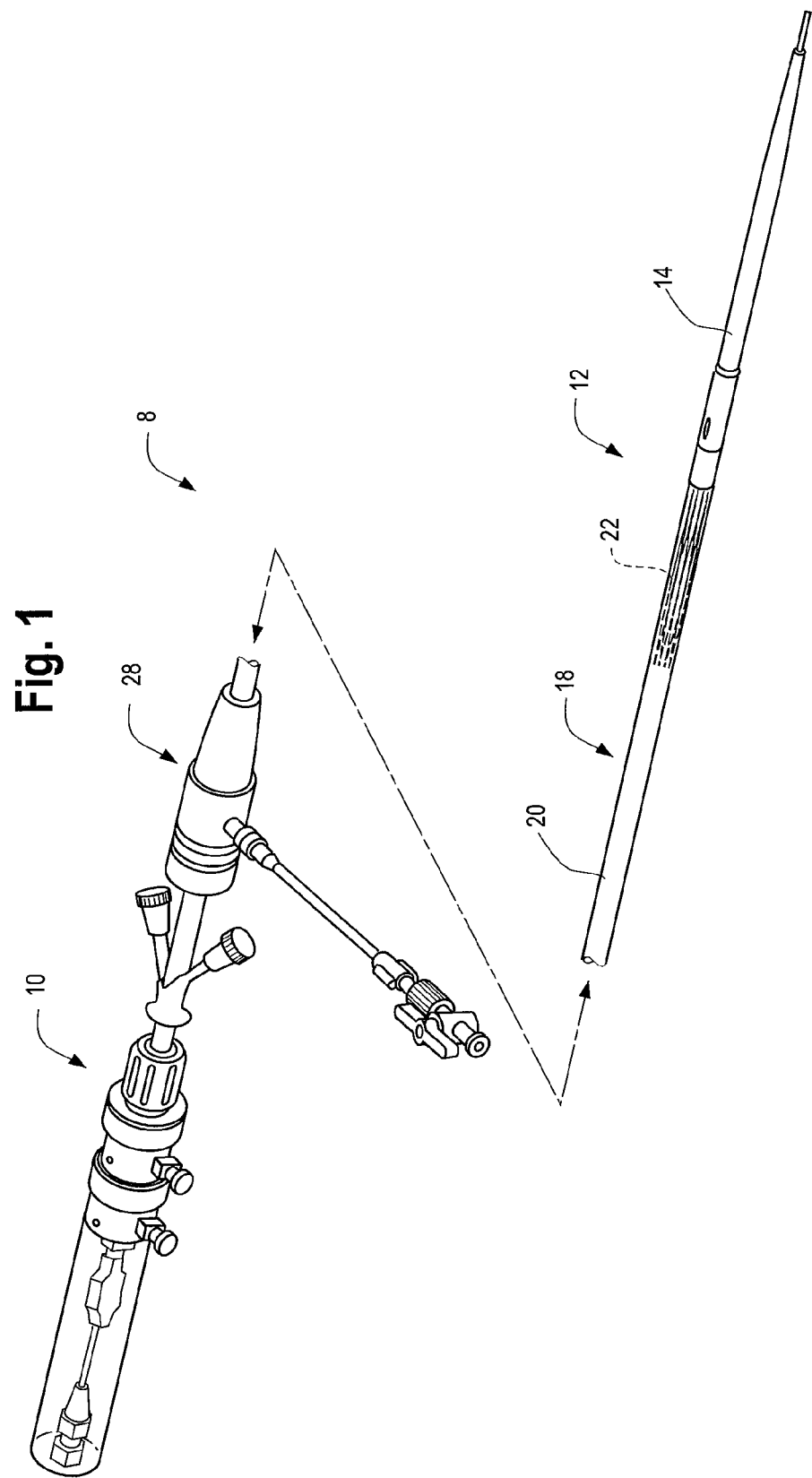
FIG. 1 shows an exemplary device for delivering a medical implant intraluminally into a patient's vasculature.
Figure 2:
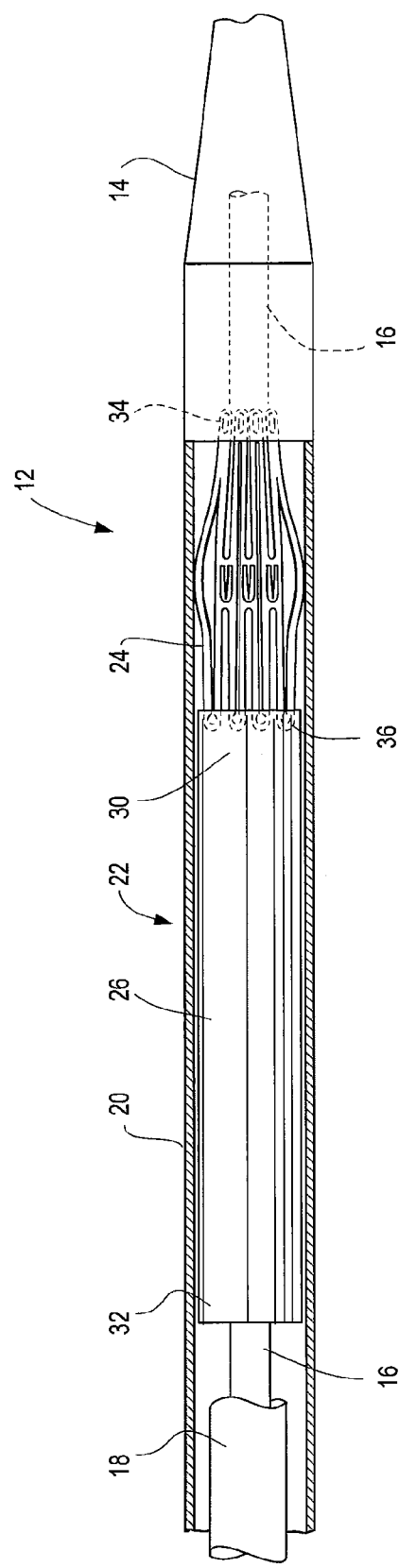
FIG. 2 is an enlarged side view of a stent graft carried by the proximal end portion of a delivery device held within an outer delivery sheath.

Referring to FIGS. 1 and 2, an example of a stent graft delivery device 8 is shown, which is useful in understanding the principles of the apparatus and methods described herein. The delivery device 8 includes a distal external manipulation section shown generally at 10 which is operated by a surgeon or clinician and a proximal end shown generally at 12 which is introduced intraluminally into a patient. During the medical procedure to deploy the stent, the proximal end 12 will travel through the vessel lumen to a desired deployment site. The external manipulation section 10, which is acted upon by a user to manipulate the device, remains outside of the patient throughout the procedure.

The proximal end 12 of the device includes a flexible dilator tip 14 having a relatively small diameter allowing for atraumatic access and delivery. An inner guide catheter 16 is fastened to the tip and is flexible so that the device can be advanced along a tortuous vessel. The inner guide catheter extends distally through the device to the external manipulation section. A pusher member 18 is mounted coaxially over and radially outside at least a portion of the guide catheter distal to the stent graft. A sheath 20 extends coaxially over the pusher member and a medical implant 22. Both the pusher member and sheath extend distally to the external manipulation region.

The medical implant 22, including a stent 24 and/or graft 26, deliverable to a target site using the delivery device 8, is retained in a compressed configuration in several ways, one of which is preferably by the sheath 20. The sheath 20 extends distally to a sheath manipulator and a hemostatic sealing unit 28 of the external manipulation section 10. The sheath manipulator and hemostatic sealing unit 28 form a seal around the pusher member 18.

Figure 3:
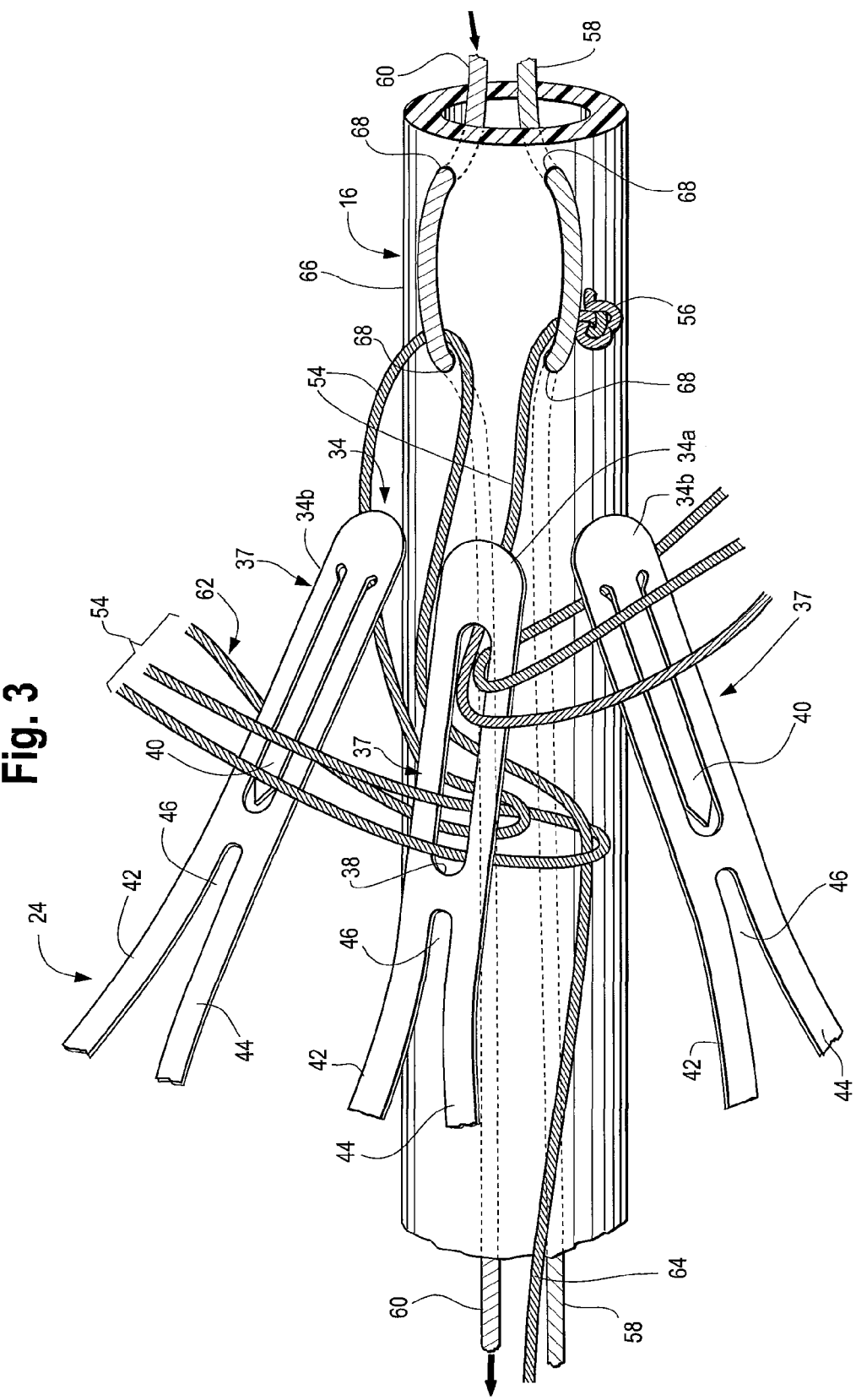
FIG. 3 is an enlarged view of one example of the proximal end portion of a stent carried by a delivery device and retained in a radially inward compressed condition.
Figure 8:
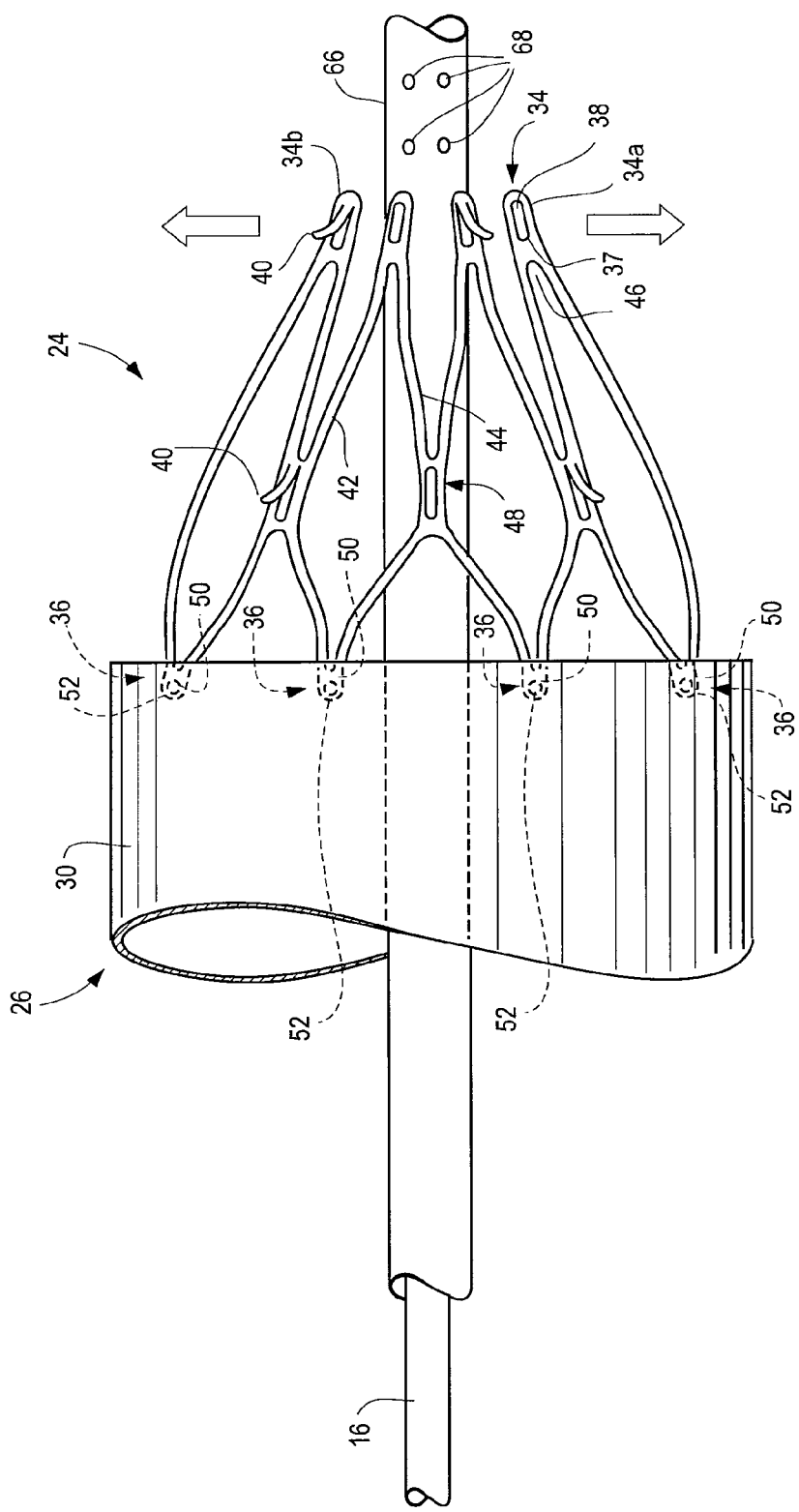
FIG. 8 is an enlarged side view of the proximal end portion of a stent-graft in a generally radially inward compressed condition and carried by a delivery device.
Figure 9:
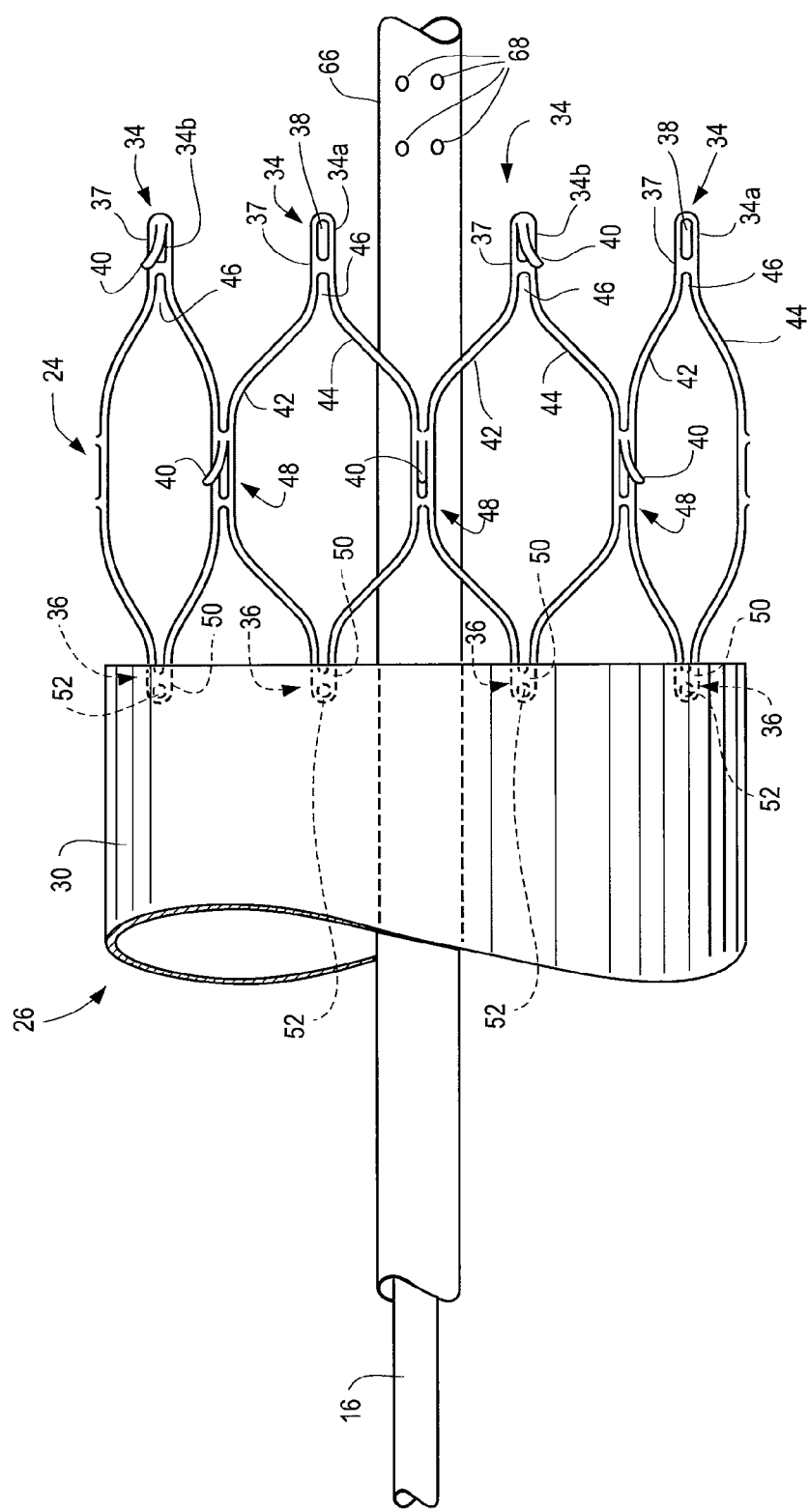
FIG. 9 is an enlarged side view of the stent-graft of FIG. 8 in a radially outward expanded configuration.

Referring now to FIGS. 2, 8 and 9 an exemplary stent graft 26 is shown. The stent graft may terminate at one or both of its proximal 30 and/or distal ends 32 in a stent 24 that is coupled to the graft material. The stent 24 may be manufactured from a continuous cylinder and may include a shape having a series of proximal apices 34 and a series of distal apices 36, though the structure is not so limited. The stent may include a series of adjacent, proximal apices 34 while the distal end of the stent may comprise a series of adjacent distal apices 36. The series of proximal apices may comprise different features. For example, as shown in FIGS. 3, 8 and 9, a first proximal apex 34a may comprise an end region 37 having an aperture 38 formed therein. A second, adjacent proximal apex 34b comprises an end region 37 having an integral barb 40 formed therein. The barbs 40 may be formed by laser cutting a desired barb shape into the end region 37, and once the desired barb shape is cut, a main body of the barb may be bent in a radially outward direction to allow for engagement of a vessel wall at a target delivery site.

Referring still to FIGS. 3, 8 and 9, the stent 24 may comprise at least one strut segment disposed between the proximal and distal apices 34, 36 respectively. Preferably, multiple angled strut segments may be disposed between corresponding proximal and distal apices. By way of example, a first proximal apex 34 extends distally and splits into first and second angled strut segments 42 and 44 respectively, thereby forming a proximal vertex 46, as shown in FIGS. 3, 8 and 9. In a compressed state, the first and second strut segments 42, 44 may be compressed such that they are substantially parallel to one another. Expansion of the stent is at least partly provided by the angled strut segments, which may tend to bow outward and away from one another in the expanded state shown in FIG. 9.

The stent may be formed from any suitable material, including an elastic material comprising a shape-memory alloy such as nickel titanium alloy (Nitinol). If the stent comprises a self-expanding material such as Nitinol, it may be heat-set into the desired expanded state. Alternatively, the stent may be made from other metals and alloys that allow the stent to return to its original, expanded configuration upon deployment, but which material does not sustain strain or damage due to compression. By way of example, other acceptable stent materials may include stainless steel, cobalt-chrome alloys, amorphous metals, tantalum, platinum, gold and titanium. The stent may also be made from non-metallic materials such as thermoplastics and other polymers.

Turning back now to FIG. 9, the stent may also comprise a transition region 48, where the angled strut segments 42, 44 meet and merge. At least one barb 40 may be disposed in at least one of the transition regions 48. The barb 40 may be integrally formed as part of the strut, or alternatively, may be an external barb that is adhered to the surface of the transition region. Like the barbs at the stent proximal end described above, the transition region barbs may be formed by laser cutting a desired barb shape into the transition regions and then bent outwardly to facilitate engagement at a target tissue site.

As shown in FIGS. 8 and 9, each of the distal apices 36 may comprise an end region 50 having an aperture 52 formed therein. The distal apices 36 may be coupled to the graft material 26, for example, using one or more sutures that are looped through the graft material and the apertures 52 of the stent. In this manner, the stent 24 may be used as an attachment stent for endovascular graft fixation. For example, the graft material 26 may overlap with an aneurysm to seal off fluid flow into the aneurysm, which the proximal end 34 of the stent 24 may extend in the proximal direction away from the graft material 26, for example, to engage a healthy portion of a vessel wall away from a diseased portion of the aneurysm. One or more additional stents may be coupled to an inner or outer surface of the graft material to help maintain patency throughout the graft material. While an exemplary stent is described and shown herein, various alternative stent designs and configurations may be used in connection with the disclosed apparatus and methods.

As mentioned above, the stent 24 has an expanded deployed state as shown generally in FIG. 9 to apply a radially outward force upon at least a portion of a vessel or duct, for example, to maintain patency within a passageway or to hold open the lumen of a graft. In the expanded state, fluid flow is allowed through a central lumen of the stent. However, prior to positioning and deployment, the stent preferably has a reduced diameter delivery configuration, or a compressed configuration as illustrated generally in FIGS. 2, 3 and 8, so that it may be advanced to the target location within a vessel or duct in the compressed state. In addition to the sheath 20 described previously, the stent 24 may also be held in a radially compressed state by one or more additional external forces or mechanisms.

As shown generally in FIG. 3, the proximal end of the stent is retained in its radially compressed form by a length of cord, tie or suture, also referred to herein as a "rip cord" 54. The rip cord 54 is preferably comprised of a flexible, small gage, high strength, low elongation material. It is also preferable that the cord material have high shear and abrasion resistance. In one example, the cord material may be a 5-0 Dyneema® manufactured by DSM High Performance Fibers and/or Spectra® manufactured by Honeywell International Inc. Other materials may include, but are not limited to, ultra high molecular weight polyethylene, braided polyester or monofilament polypropylene.

Figure 4:
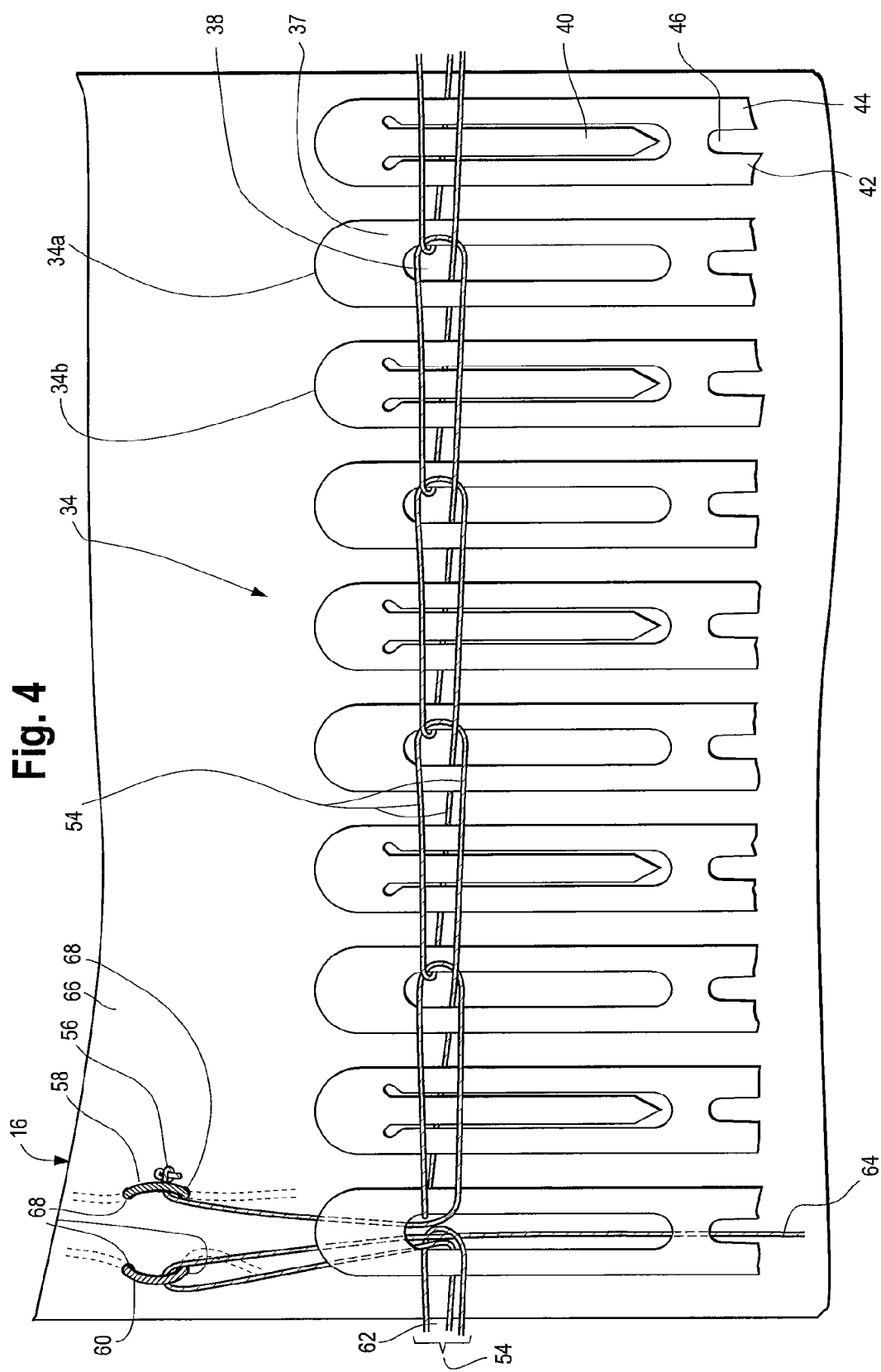
FIG. 4 is an enlarged side view of one example of a restraining device woven through the proximal apices of the proximal end portion of a stent and held in place against a delivery device by trigger wires.

As shown in FIGS. 3 and 4 the rip cord 54 is stitched or woven through one or more of the apertures 38 located near or at the end region 37 of the proximal apices 34. The rip cord 54 is preferably "chain stitched" around the stent proximal end through the aperture 38 of one apex, and again through the aperture 38 of another apex, in a continuous pattern around at least a portion of or the entire circumference of the stent 24. However, the rip cord may weave or loop through the apices 34 and/or wrap around the stent body in any suitable pattern in order to releasably secure the stent proximal end in a compressed condition. As shown in FIGS. 3 and 4 for example, the rip cord 54 is stitched in a pattern that alternates looping the cord through every other apex 34a, thus skipping or passing over the immediately adjacent apex 34b having a barb 40. If desired, the rip cord stitching could be continued to the second row of barbs 40 at or near the transition region 48 of the stent and retain the barbs such that no barbs are expanded when the sheath 20 is withdrawn during deployment.

A first end or portion 56 of the rip cord 54 may be secured or anchored to a portion of the inner catheter 16. In order to anchor the rip cord to the inner catheter, the cord may be adhered, knotted, tied and/or looped under a portion of at least one trigger wire 58 extending along the surface of the inner catheter 16 or alternatively, an end of the rip cord may be threaded through one or more apertures or eyelets formed in the inner catheter. As shown in exemplary FIGS. 3 and 4, one end 56 of the rip cord is knotted. A portion of the rip cord that extends from this "retaining knot" is held securely in place against the surface of the inner catheter 16 by one of the trigger wires 58, and the retaining knot prevents the end 56 of the rip cord from slipping out from underneath the trigger wire 58. The retaining knot 56 may, in one non-limiting example, be a releasable knot such as a "clove hitch knot" tied around trigger wire 58 so that upon removal of the trigger wire 58, the retaining knot 56 automatically releases or unties. However, the rip cord may be secured to the inner catheter in any suitable manner, but in such a way that the end of the rip cord can be released from the inner catheter anchor upon removal of a trigger wire and/or upon application of a pulling force upon the rip cord such as manual pulling by a physician and/or through an appropriate control element or handle at the external manipulation section 10 of the delivery device 8.

The rip cord 54 extends from the knotted end 56, which is anchored to the inner catheter, and is then tied, woven and/or threaded around at least a portion of the outer circumference of the stent proximal end 34 as described above. FIGS. 3 and 4 illustrate that the rip cord 54 has been woven around the circumference of the stent proximal end 34. The weave then terminates in a final "stitch" 62. As FIGS. 3 and 4 show, the rip cord extends proximally from stitch 62 and is looped underneath a portion of a second trigger wire 60. The second trigger wire 60 holds that portion of the rip cord securely in place against the surface of the inner catheter 16. The remaining length 64 of the rip cord then extends in a distal direction from the point where it is anchored against the inner catheter, through the interior of the stent and graft body, to a point where it terminates at or near the external manipulation section 10 of the delivery device 8 as shown in FIGS. 3 and 4.

Figure 11:
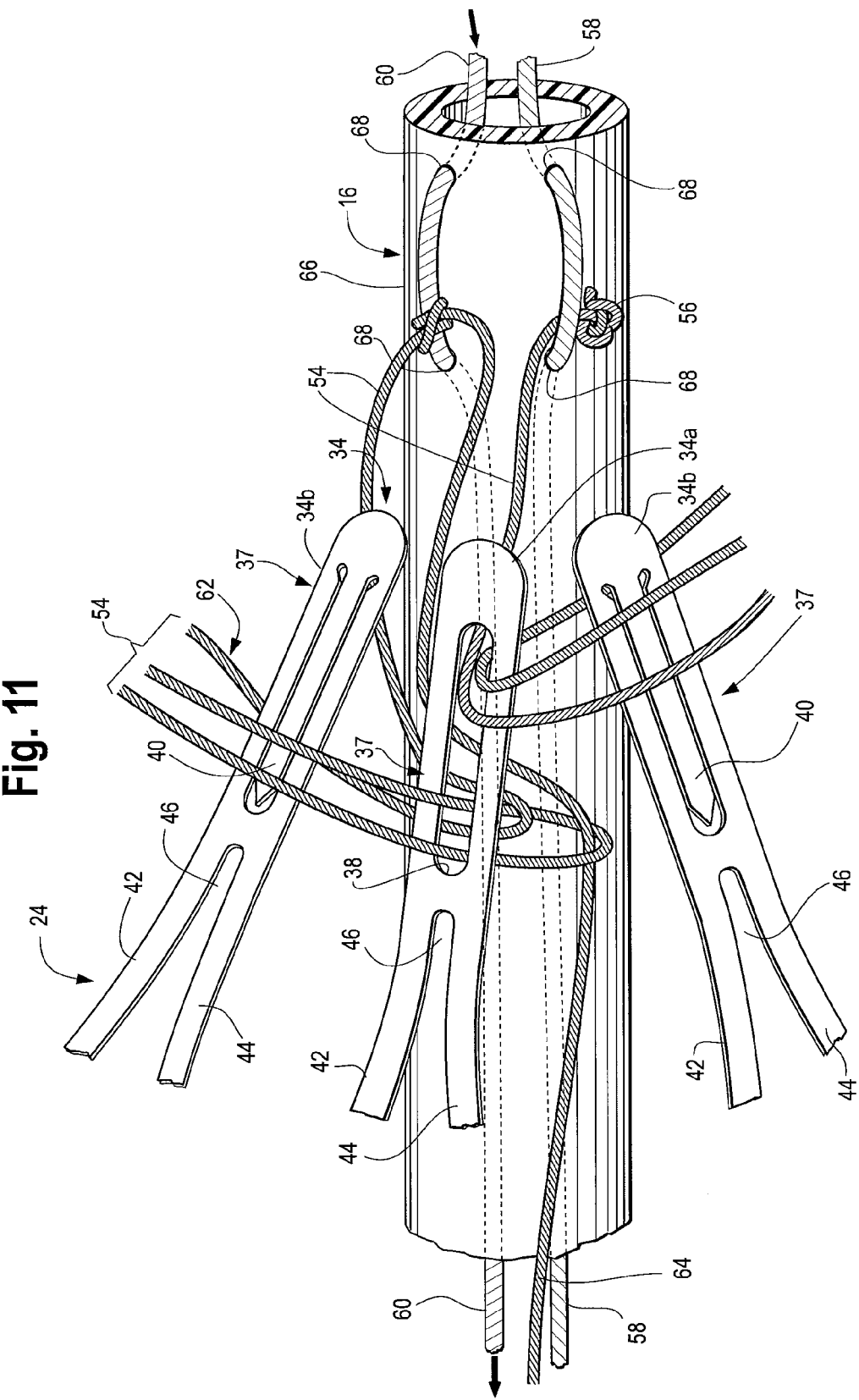
FIG. 11 is an enlarged view of another example of the proximal end portion of a stent carried by a delivery device and retained in a radially inward compressed condition.
Figure 12:
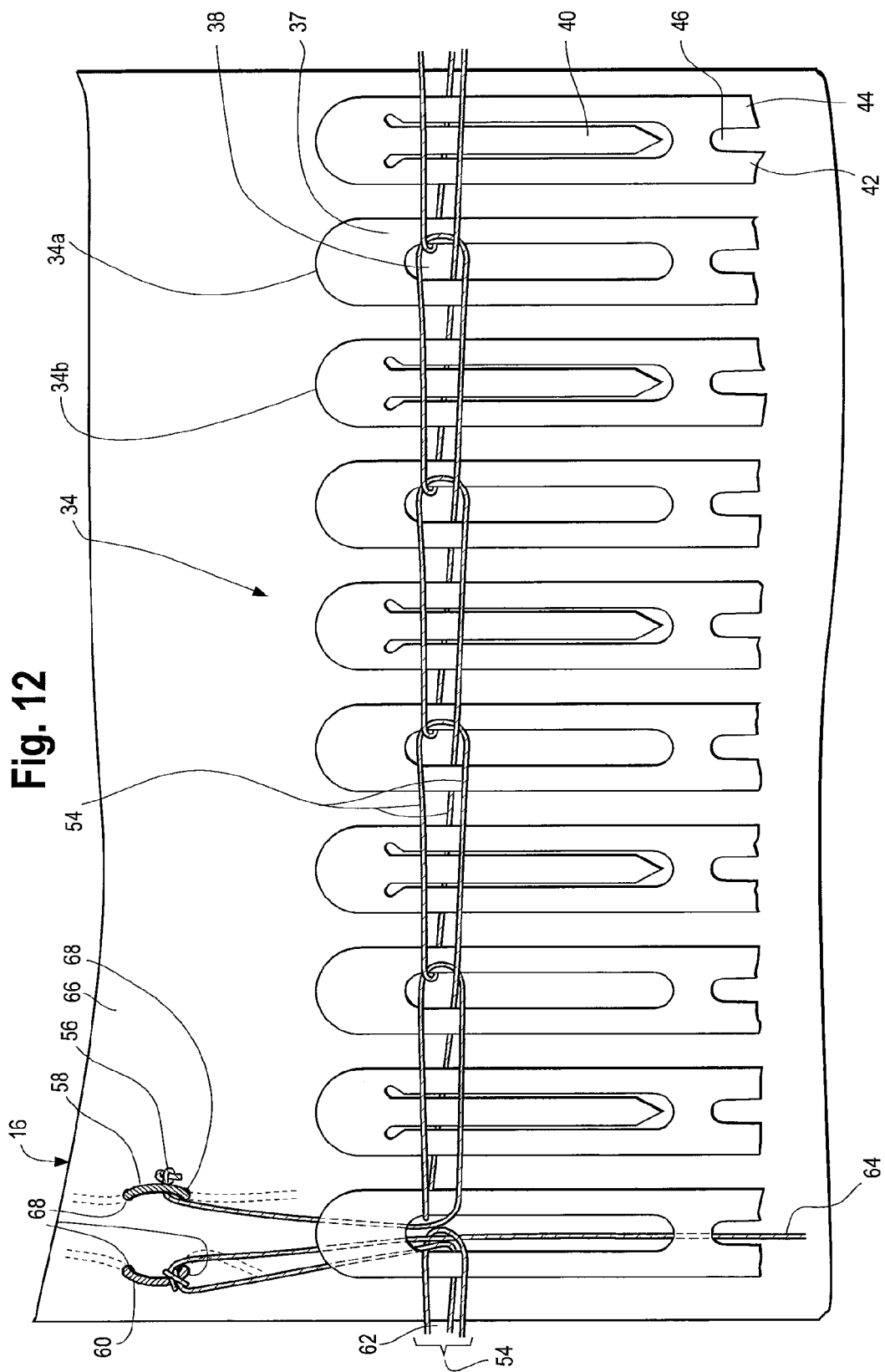
FIG. 12 is an enlarged view of another example of a restraining device woven through the proximal apices of the proximal end portion of a stent and held in place against a delivery device by trigger wires.

Alternatively, as shown in FIGS. 11 and 12, the rip cord may extend in a proximal direction from stitch 62 where it is then releasably secured to a portion of the second trigger wire 60. For example, the rip cord may be knotted, such as by a "clove hitch knot" or any other suitable releasable mechanism or knot, around second trigger wire 60 (rather than simply looped underneath trigger wire 60 as shown in FIGS. 3 and 4). The second trigger wire 60 holds that portion of the rip cord securely in place against the surface of inner catheter 16. Releasably securing or knotting the rip cord 54 around trigger wire 60 substantially prevents or eliminates the rip cord from sliding laterally underneath the trigger wire 60. It also substantially prevents or eliminates the rip cord 54 from sliding distally when the sheath 20 is withdrawn in that direction, thus preventing tension from forming in the rip cord 54, which tension would otherwise extend distally along the length of the cord from the trigger wire 60 to where it terminates in the external manipulation portion or handle 10. In addition, releasably securing or knotting the rip cord 54 around trigger wire 60 also allows the knot to automatically untie and release upon removal of the trigger wire 60, thus, substantially reducing or eliminating the possibility that any such knot could become snagged or snared when the rip cord is pulled in a distal direction during removal from the device 8.

Preferably, as shown in FIGS. 3, 4, 11 and 12, the rip cord 54 substantially surrounds the outer circumference of the proximal stent end 34. Thus, upon pulling the rip cord taut or otherwise drawing the cord securely around the stent proximal end, the multiple apices 34a and 34b are also drawn radially inward into a compressed orientation. As such, the rip cord maintains the stent in a pre-deployment compressed configuration, thus resisting the generally outward force created by the stent apices which tend to want to return to the original expanded configuration.

It is also contemplated that a second stent (not shown) at the distal end 32 of the stent graft 26 may be radially restrained by a rip cord in a manner similar to that previously described in connection with the proximal stent restraint. A rip cord securing a stent at the distal end 32 of the graft 26 may be comprised of the same length of material that makes up the rip cord securing the proximal end stent. Alternatively, a second or separate piece of cord or material may be used to radially constrain a distal end stent. As such, the endovascular graft would have both proximal and distal fixation to the delivery device to radially constrain the graft at both ends until deployment.

In previously-known stents, one or more trigger wires may run longitudinally along the internal delivery catheter and through the inside of the stent body. To secure the stent in the compressed condition for delivery, the trigger wire may be woven from the inside to the outside of the stent. For example, the wire may weave through one or more apices at the stent proximal end, and then secured to a portion of the delivery device. As mentioned above, this arrangement may be associated with several drawbacks. In one example, the weaving of a trigger wire up and over the stent body and the coupling of the trigger wire to the delivery device requires substantial radial flexure and bending of the wire to accommodate the shape and external diameter of the stent, even when the stent is in a compressed condition. There is also friction at the points of contact between the trigger wire and the surface of the stent. As a result, the "deployment force" that is required for a physician to be able to release and withdraw the trigger wire during deployment is undesirably high. However, as explained below, the described apparatus and methods utilize a different approach which advantageously avoids such drawbacks.

In particular, referring now to FIG. 3 at least one trigger wire, and preferably two trigger wires 58, 60, may extend along the length of the inner catheter 16 and through the interior of the stent 24 and stent graft 26. The trigger wires may simply run alongside or parallel to the inner catheter 16, but more preferably, the trigger wires run underneath a sheath or sleeve 66 that covers the inner catheter 16. If the trigger wires run underneath such a sleeve, the sleeve 66 preferably includes one or more apertures or openings 68 to allow at least a proximal portion of the trigger wires to emerge, exit or otherwise pass out of the sleeve. Preferably, as shown in exemplary FIGS. 3 and 4, there are two pairs of apertures 68, with each trigger wire 58, 60 passing through one of the respective pairs of apertures. Accordingly, a proximal portion of the trigger wire, after emerging from an aperture 68 in the sleeve 66 as shown in FIGS. 3 and 4, may be looped or woven over a portion of the rip cord 54, near the stent proximal end. The proximal end of the trigger wire may be coupled to or otherwise secured to the delivery device. In one example, after looping over the rip cord 54, the end of the trigger wires 58, 60 may be inserted into a second opening or aperture 68 in the sleeve 66 covering the inner catheter 16 so that the trigger wire passes back under the sleeve and is held by friction fit between the inner catheter 16 and the dilator tip 14.

Preferably, the trigger wires are not coupled to, disposed though or woven over the proximal stent apices 34 or any other portion of the material which comprises the stent 24. As shown, the trigger wires 58, 60 are only woven over a portion of the rip cord 54 between adjacent stent apices 34a and 34b, with little or no contact with the apices, as best seen in FIG. 3, thus reducing and potentially eliminating any friction that would otherwise exist between the trigger wires 58, 60 and the stent material. In this way, excessive radial flexure of the trigger wires is also reduced or eliminated, as the trigger wires do not have to bend up and over the stent apices 34a and 34b at the proximal end. As a result, the deployment force required for the physician to pull the trigger wires 58, 60 distally during release and deployment is very low.

Weaving the trigger wires 58 and 60 up and over a portion of the rip cord 54 near the stent proximal end 34 provides inward radial force against the rip cord by the trigger wires, which, in turn, helps to secure the rip cord 54 against the inner catheter 16. More particularly, the first and second trigger wires, respectively, hold the respective ends of the circumferential stitching of the rip cord against the surface of the inner catheter. As such, the rip cord is held in a relatively taut condition around the exterior surface of the stent proximal end, thus holding the proximal end in a radially inward compressed condition against the inner catheter. In addition, the trigger wires 58, 60, by holding or otherwise securing the rip cord 54 against the inner catheter, secures the stent 24 and graft 26 in a particular longitudinal position relative to the inner catheter 16, and resists longitudinal sliding or movement of the stent that may otherwise occur during delivery, positioning and/or deployment. Advantageously, the trigger wires 58, 60 are essentially relieved of the burden of having to also resist radial outward expansion of the stent 24, because it is primarily the rip cord 54 that provides such radial restraint of the proximal apices 34a and 34b. As such, there is less strain, tension and/or force loads that would otherwise lie solely upon the trigger wires (e.g. if the trigger wires were to bear the burden of resisting both radial and longitudinal stent graft movement) thus, reducing the deployment force necessary to remove and withdraw the trigger wires during deployment.

Longitudinal movement of the stent 24 and graft is highly undesirable because such movement, especially during delivery and/or deployment, may result in inaccurate and improper positioning of the stent within a body passage or vessel, which, after deployment, may be difficult or even impossible to reposition and possibly cause vessel damage. Unwanted longitudinal movement of the stent is likely to occur, for example, during withdrawal of the sheath 20. More particularly, the distal pulling force that is required to withdraw the sheath 20 from the stent and graft during deployment may cause the entire stent and graft to slide in a distal direction as the sheath is pulled. Even when one or more trigger wires are used to resist such movement, the pulling force created by the sheath may still cause the stent 24 to slide in a distal direction. Such movement, even if minimal, is undesirable. Thus, in addition to the use of one or more trigger wires 58, 60 to resist longitudinal movement as described above, other mechanisms for reducing and even substantially eliminating unwanted longitudinal movement of the stent 24 and graft 26 may be employed. Such other mechanisms may be used alone or in combination with the other mechanisms described herein.

Figure 10:
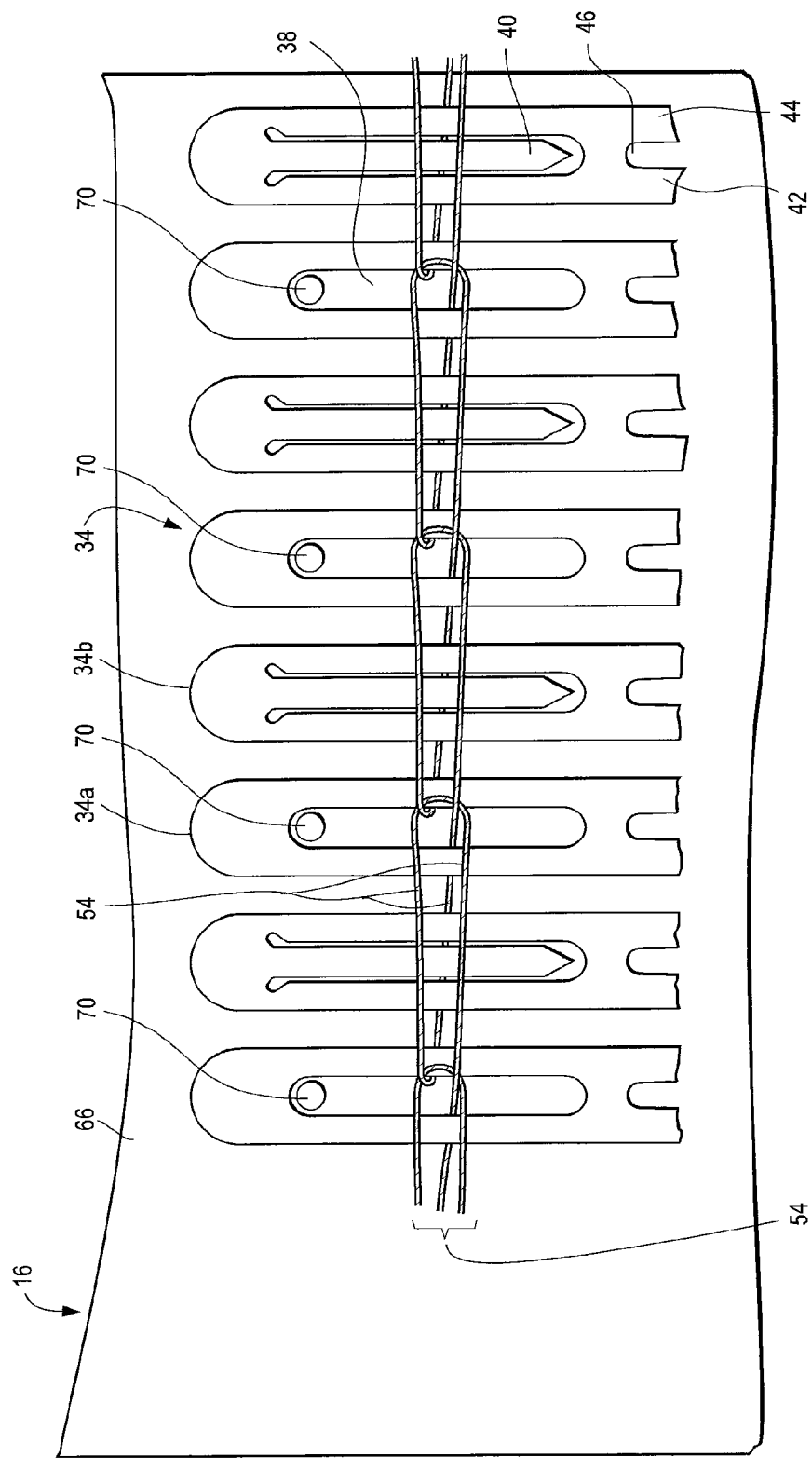
FIG. 10 is an enlarged side view of the proximal apices of a stent retained radially inwardly by a restraining device and retained in a longitudinal position relative to a delivery device by a series of radially outwardly extending posts.

For example, as shown in FIG. 10, one or more protrusions 70 may extend from the inner catheter 16 to engage a portion of the stent 24 or graft 26. The protrusions 70 may be pegs, posts, hooks, supports or other structures which preferably extend radially outwardly from the inner catheter 16. As shown in FIG. 10, a ring or series of adjacent posts 70 extend outwardly from the inner catheter at a position just distal to the stent proximal end 34. The posts are preferably of a sufficient length such that they extend into and/or through one or more apertures 38 in the stent apices 34a when the stent is restrained in a radially compressed predeployment configuration. Thus, when the sheath 20 is pulled in a distal direction during withdrawal, one or more of the posts 70 engage the proximal most portion of the aperture 38, thus preventing unwanted longitudinal movement or sliding of the stent 24 in a distal direction. Once the proximal end of the stent has been deployed such that the proximal apices have assumed a radially outward expanded configuration as shown in FIG. 9 for example, the posts 70 will no longer extend through the apertures 38 nor engage any other portion of the stent or graft. Accordingly, the inner catheter 16 can be freely withdrawn, when desired, in a distal direction without the post snagging or causing interference with the stent or graft.

An exemplary method of delivering and deploying an implantable medical device such as an endovascular graft in accordance with the apparatus and methods described herein are now provided. Once the proximal end 12 of the delivery device is in a desired position within a patient's vessel, the sheath 20 is pulled distally to withdraw it from the proximal end 34 of the stent and expose the proximal end 34. It can be seen in FIGS. 3, 4, 11 and 12 for example, that the proximal end 34 is still radially constrained by the rip cord 54, while the distal end of the stent 36 and graft 26 are still retained within the sheath. The proximal end of the stent will only be released to its expanded configuration once the rip cord has been "unzipped" or released.

To initiate deployment, the trigger wires are preferably released sequentially and removed by the physician to loosen and unzip the rip cord, which allows the proximal end of the stent to expand radially outwardly and engage the vessel wall. Preferably, the first trigger wire is released, for example, by manipulating one or more actuators on the external manipulation section 10 of the device 8 which allows a physician to control accurate deployment of the proximal end 34 of the stent. The physician may use the external manipulation section 10 of the device to pull the trigger wire distally until it is released. If the proximal end of the trigger wire is held by friction fit between the inner catheter 16 and the dilator tip 14 for example, the physician would apply sufficient distal pulling force to release the wire from where it was frictionally held and continue to pull it in a distal direction until an initial portion of the rip cord 54 is released. If the rip cord 54 were releasably secured (such as by a "clove hitch knot") to trigger wire 60 as shown in FIG. 12, removal of the trigger wire 60 would allow the rip cord to automatically untie.

Figure 5:
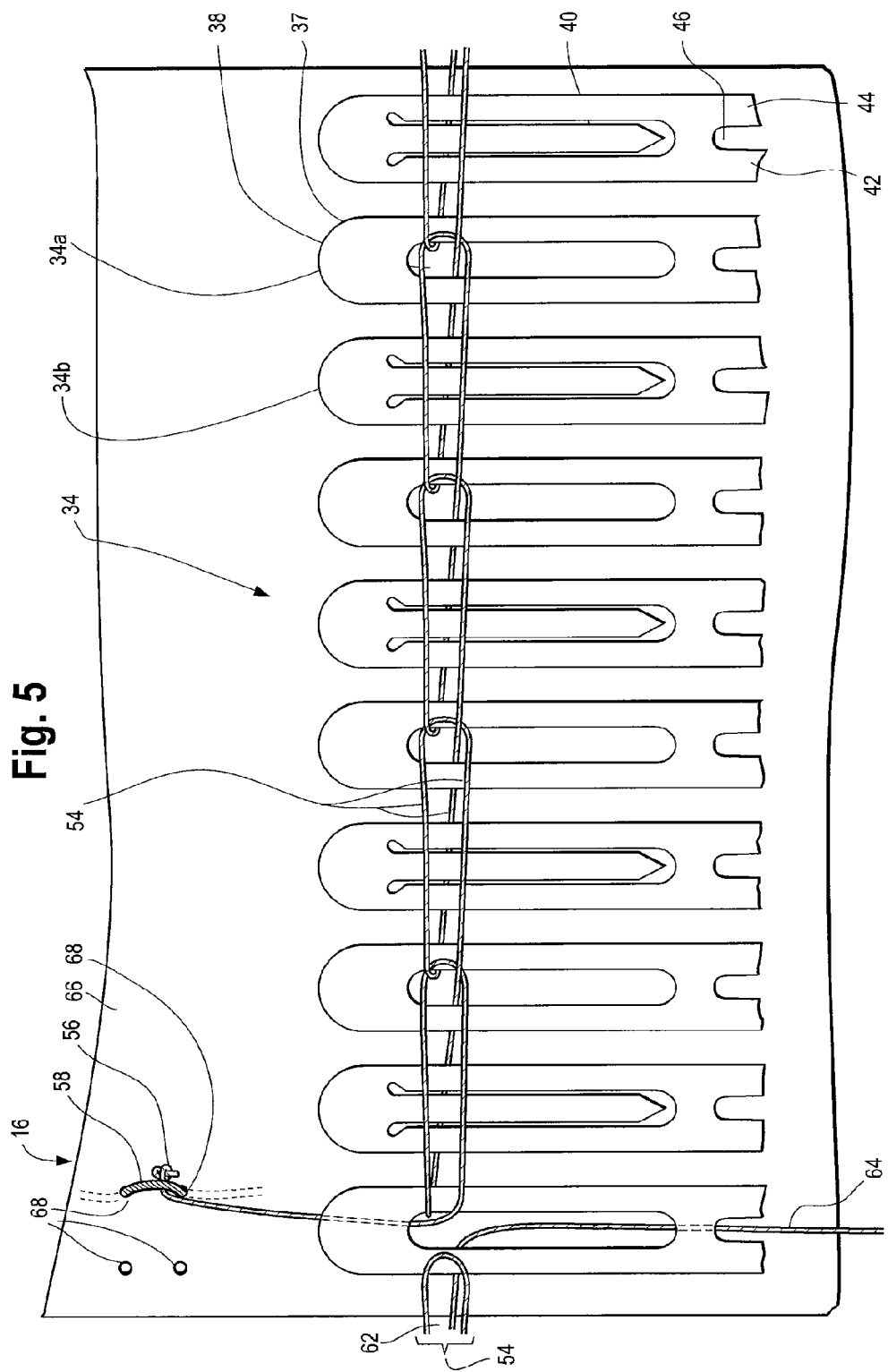
FIG. 5 is an illustration of the enlarged side view of FIG. 4 with one of the trigger wires removed.
Figure 6:
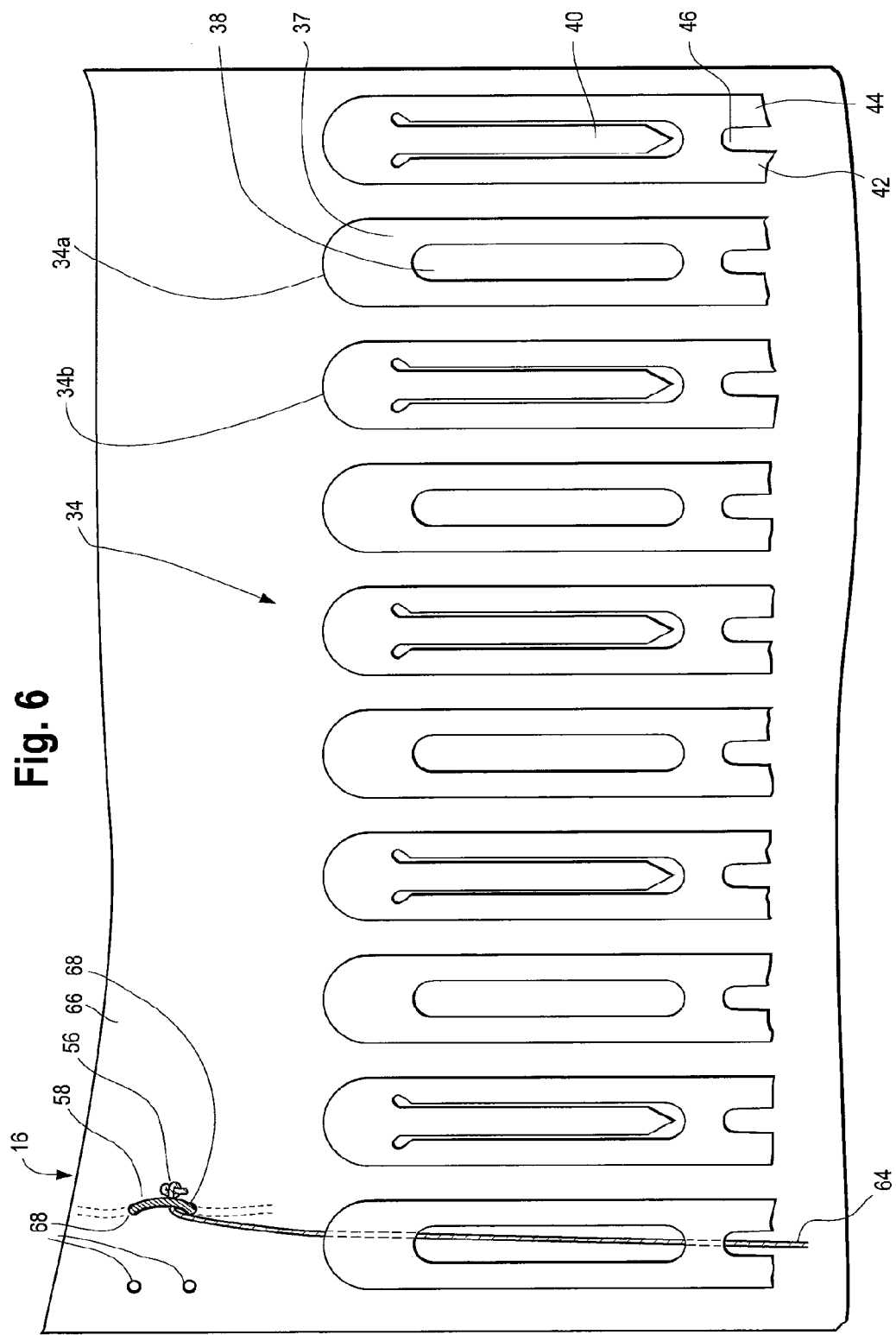
FIG. 6 is an illustration of the enlarged side view of FIGS. 4 and 5 with the restraining device released from the proximal stent apices.

More particularly, as shown in FIG. 5, removal of the one trigger wire releases the portion of the rip cord that was looped underneath (or, alternatively, as shown in FIG. 12, was releasably knotted) and anchored to the delivery catheter 16 by trigger wire 60. Releasing the initial anchored portion of the rip cord allows the "stitch" 62 of the rip cord to unzip, such that the subsequent stitches through the stent apertures 38 loosen and unravel as illustrated in FIG. 6. The outward radial force of the stent apices 34a and 34b assist in unzipping the rip cord 54 from the proximal stent end 34. With the rip cord unzipped and no longer retaining the proximal apices in a constrained configuration as FIG. 6 shows, deployment of the proximal stent end is accomplished as the apices 34a and 34b smoothly and accurately assume a radially outward expanded configuration within the vessel.

Figure 7:
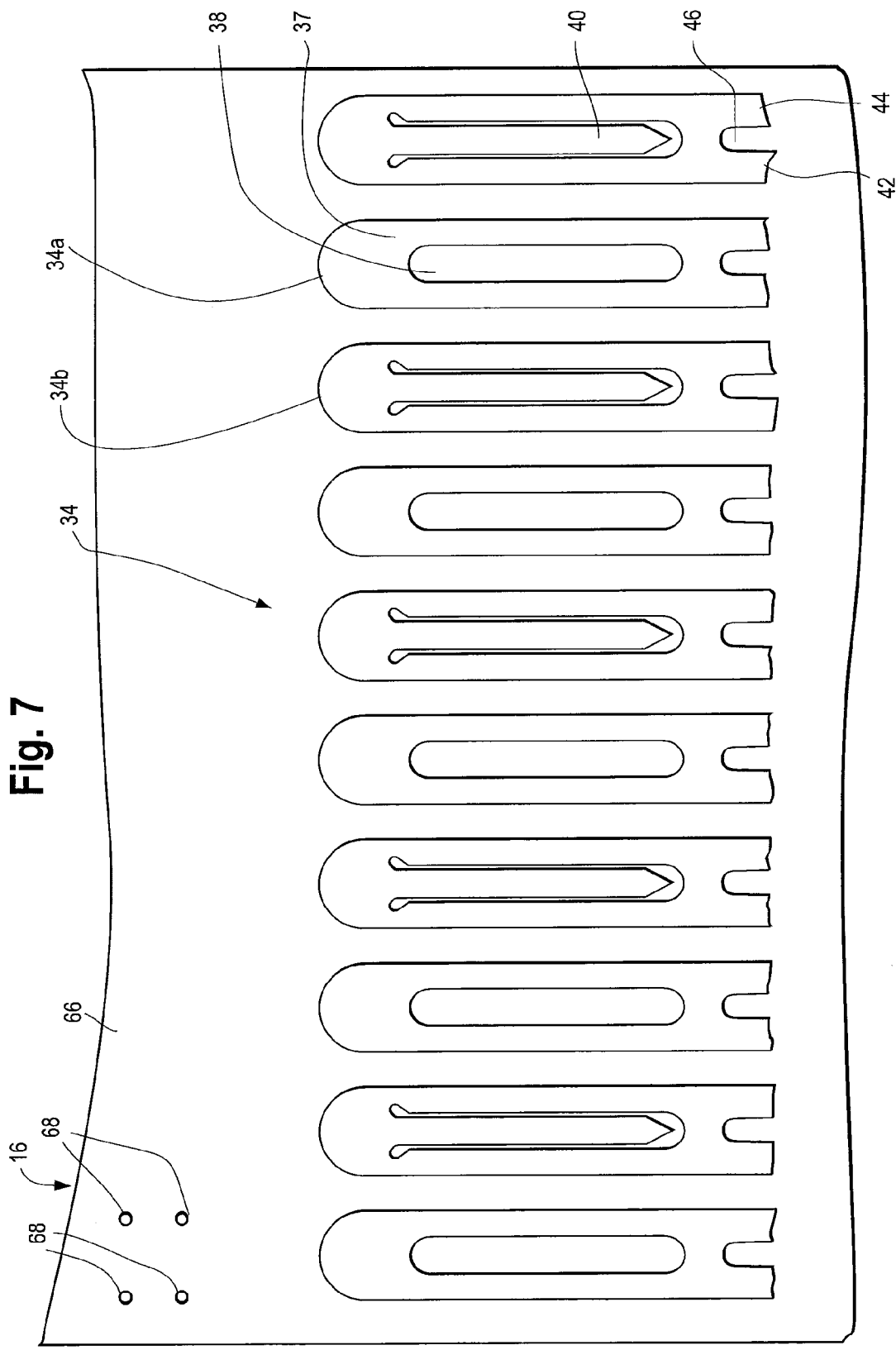
FIG. 7 is an illustration of the enlarged side view of FIGS. 4-6 with the second trigger wire removed.

Next, as shown in FIGS. 6 and 12, an end portion 56 of the rip cord 54 is still retained and/or anchored against the inner catheter 16 by the second trigger wire 58. More particularly, a retaining knot 56 at one end of the rip cord holds the end of the cord securely underneath the trigger wire 58. Preferably, trigger wire 58 is then removed in a manner similar to the removal of the first trigger wire 60. For example, the physician may apply a distal pulling force, either manually or by actuation of one or more controls at the external manipulation section 10 of the delivery device, to dislodge and release the second trigger wire 58. Again, if the proximal end of the second trigger wire is held by friction fit between the inner catheter 16 and the dilator tip 14 in a manner similar to the first trigger wire, the physician would apply sufficient distal pulling force to release the wire from where it was frictionally held and continue to pull it in a distal direction until the trigger wire 58 is fully released. Removal of the second trigger wire 58 releases the retaining knot 56 (which may, in one example, be a releasable knot tied around trigger wire 58, including a "clove hitch knot") such that the rip cord is no longer held tightly against the inner catheter 16, and, upon continued withdrawal of the second trigger wire 58 in a distal direction, the rip cord 54 may also be completely removed from the delivery device as shown in FIG. 7.

If, for any reason, the trigger wires 58, 60 fail to release rip cord 54 and/or the rip cord fails to properly unzip or becomes snared within the delivery device, it is contemplated that the stent 24 may be expanded by other mechanical forces. For example, the stent 24 and graft 26 may be expanded from within by a balloon catheter or any other suitable device for creating forces sufficient for expanding the graft to force the rip cord to unzip, thus allowing the stent and graft to still expand accurately in the desired position within the vessel.

With the proximal end of the stent 34 deployed and engaged with the vessel at the desired location and the trigger wires 58 and 60 and rip cord 54 removed, the sheath 20 may be distally retracted even further to expose a greater portion of the stent graft. Continued withdrawal of the sheath 20 allows the stent graft to become fully deployed within the patient's vessel. The delivery device 8 and/or any remaining guide wires or instruments may be removed from the vasculature to complete the deployment procedure.

Throughout this specification, unless the context requires otherwise, the words "comprise" and "include" and variations such as "comprising" and "including" will be understood to imply the inclusion of an item or group of items, but not the exclusion of any other item or group items.

While various examples of the invention have been described, it will be apparent to those of ordinary skill in the art that many more examples and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. An apparatus for deploying a stent comprising:
a stent delivery device having a proximal end portion and a distal end portion;
at least one stent carried on the proximal end portion of the delivery device, the stent having both an expanded configuration and a radially inward compressed configuration, the stent comprising a proximal end and a distal end;
a restraining device comprising a releasable pattern circumferentially engaged with the stent proximal end portion and exerting a force on the stent in a radially inward direction, the restraining device releasably retaining the proximal stent end in the radially inward compressed condition;
at least one release mechanism comprising a proximal end portion and a distal end portion, wherein the proximal end portion of the release mechanism is releasably coupled to the restraining device for selectively releasing the restraining device from the proximal stent end such that upon removal of the at least one release mechanism, the restraining device circumferentially disengages and the stent proximal end assumes the radially outward expanded position,
wherein the restraining device comprises a rip cord that is raveled in a continuous chain stitch pattern of a plurality of chain stitches around at least a portion of the stent proximal end and weaves through a plurality of apertures at the stent proximal end and around the circumference of the stent.

2. The apparatus of claim 1 wherein a tubular graft prosthesis is attached to at least a portion of the stent distal end.

3. The apparatus of claim 1 wherein the proximal stent end comprises a plurality of apices.

4. The apparatus of claim 3 wherein at least one of the plurality of proximal apices comprise an aperture formed therein and wherein the restraining device is woven, raveled or stitched through the at least one aperture.

5. The apparatus of claim 1 wherein the restraining device comprises a first contracted position and a second loosened position.

6. The apparatus of claim 5 wherein the proximal end of the stent is maintained in a radially inward compressed configuration when the restraining device is in the first contracted position.

7. The apparatus of claim 5 wherein the proximal end of the stent assumes a radially outward expanded configuration when the restraining device is in the second loosened position.

8. The apparatus of claim 1 wherein the restraining device comprises an elongated material, cord, string, suture, tie, wire, line or thread.

9. The apparatus of claim 1 wherein the chain stitch pattern around at least a portion of the stent proximal end circumferentially disengages by unraveling the plurality of chain stitches.

10. The apparatus of claim 1 wherein the release mechanism comprises a first release mechanism and a second release mechanism.

11. The apparatus of claim 10 wherein the first release mechanism comprises a first trigger wire and the second release mechanism comprises a second trigger wire.

12. The apparatus of claim 11 wherein one of the first and second trigger wires releasably secures a portion of the restraining device to the stent delivery device.

13. The apparatus of claim 11 wherein the restraining device comprises a circumferential suture and one of the first and second trigger wires is releasably coupled to a first end portion of the circumferential suture and the second of the first and second trigger wires is releasably coupled to a second end portion of the circumferential suture to maintain the suture in a substantially taut condition, thereby maintaining the stent proximal end in a radially inward compressed condition.

14. The apparatus of claim 12 wherein the other of the first and second trigger wires releasably secures another portion of the restraining device to the stent delivery device.

15. The apparatus of claim 1 wherein a guide catheter extends at least partially between the proximal and distal end portions of the delivery device and the stent is mounted coaxially over and radially outside a portion of the guide catheter.

16. The apparatus of claim 15 wherein the guide catheter further comprises at least one radially outwardly extending protrusion for engaging the proximal end portion of the stent when the proximal stent end is in the radially inwardly compressed configuration.

17. The apparatus of claim 16 wherein proximal end portion of the stent comprises a plurality of apices and the protrusion engages an aperture formed in at least one of the apices to restrain longitudinal movement of the stent relative to the delivery device.

18. An apparatus for deploying a stent comprising:
a stent delivery device having a proximal end portion and a distal end portion;
at least one stent carried on the proximal end portion of the delivery device, the stent having both an expanded configuration and a radially inward compressed configuration, the stent comprising a proximal end and a distal end;
a restraining device comprising a releasable pattern circumferentially engaged with a plurality of apices at the stent proximal end portion and exerting a force on the stent in a radially inward direction, the restraining device releasably retaining the proximal stent end in the radially inward compressed condition, wherein the restraining device engages the stent proximal end portion in a pattern that alternates through every other apex;
at least one release mechanism comprising a proximal end portion and a distal end portion, wherein the proximal end portion of the release mechanism is releasably coupled to the restraining device for selectively releasing the restraining device from the proximal stent end such that upon removal of the at least one release mechanism, the restraining device circumferentially disengages and the stent proximal end assumes the radially outward expanded position, wherein the restraining device circumferentially disengages by unraveling.

19. A method for deploying an endovascular prosthesis comprising the steps of:
   a. inserting a delivery device carrying the prosthesis into the lumen of a body passage, the prosthesis having at least a proximal end retained in a radially inwardly compressed delivery condition by a restraining device comprising a releasable pattern circumferentially engaged around at least a portion of the stent proximal end;
   b. withdrawing a sheath from the delivery device to expose at least a portion of the prosthesis;
   c. withdrawing a first release mechanism from the delivery device to facilitate the circumferential disengagement and release of the restraining device from the proximal end of the prosthesis to deploy the prosthesis in a radially outwardly expanded position;
   d. withdrawing the restraining device from the body passage; and
   e. retracting the delivery device from the body passage, wherein the restraining device comprises a rip cord that is raveled in a continuous chain stitch pattern of a plurality of chain stitches around at least a portion of the stent proximal end and weaves through a plurality of apertures at the stent proximal end and around the circumference of the stent,
   and wherein the restraining device circumferentially disengages by unraveling.

20. The method of claim 19 wherein the releasable pattern comprises a single chain stitched thread raveling or chain-stitching of the restraining device and wherein the restraining device circumferentially disengages by unraveling.

* * * * *